(12) United States Patent
Scott-Young

(10) Patent No.: US 10,687,959 B2
(45) Date of Patent: Jun. 23, 2020

(54) SPINAL FIXATION SYSTEM

(71) Applicant: PRISM SURGICAL DESIGNS PTY LTD, Queensland (AU)

(72) Inventor: Matthew Norman Scott-Young, Queensland (AU)

(73) Assignee: PRISM SURGICAL DESIGNS PTY LTD, Red Hill (AU)

( * ) Notice: Subject to any disclaimer, the term of this patent is extended or adjusted under 35 U.S.C. 154(b) by 315 days.

(21) Appl. No.: 15/556,838

(22) PCT Filed: Jan. 20, 2016

(86) PCT No.: PCT/AU2016/050025
§ 371 (c)(1),
(2) Date: Sep. 8, 2017

(87) PCT Pub. No.: WO2016/205870
PCT Pub. Date: Dec. 29, 2016

(65) Prior Publication Data
US 2018/0049888 A1 Feb. 22, 2018

(30) Foreign Application Priority Data

Jun. 23, 2015 (AU) .............................. 2015902419

(51) Int. Cl.
*A61F 2/44* (2006.01)
*A61B 17/70* (2006.01)
(Continued)

(52) U.S. Cl.
CPC ........ *A61F 2/4455* (2013.01); *A61B 17/7059* (2013.01); *A61B 17/8872* (2013.01); *A61B 17/1757* (2013.01); *A61F 2002/30578* (2013.01)

(58) Field of Classification Search
CPC .................................................... A61F 2/4455
See application file for complete search history.

(56) References Cited

U.S. PATENT DOCUMENTS 8,480,747 B2 * 7/2013 Melkent ................. A61F 2/442
623/17.11
2007/0270965 A1 * 11/2007 Ferguson ........... A61B 17/7059
623/17.11
(Continued)

FOREIGN PATENT DOCUMENTS

WO  2010107692   9/2010
WO  2014188280   11/2014

OTHER PUBLICATIONS

PCT Search Report & Written Opinion dated Mar. 2, 2016 for PCT/AU2016/050025 filed on Jan. 20, 2016 entitled A Spinal Fixation System (Applicant: Prism Surgical Design Pty Ltd).

*Primary Examiner* — Nicholas W Woodall
(74) *Attorney, Agent, or Firm* — Knobbe, Martens, Olson & Bear, LLP

(57) ABSTRACT

A spinal fixation system, the system including: an alignment assembly comprising: a fastening element; and a mating element configured to receiving the fastening element thereover and having a releasable connector, a fixation assembly comprising: a plate having an aligning aperture that allows the mating element to be received therethrough; and an implant configured to be received between adjacent vertebrae and releasably connect with the releasable connector, wherein the fastening element is configured to move along the mating element to engage with the plate.

11 Claims, 4 Drawing Sheets

(51) Int. Cl.
*A61B 17/88* (2006.01)
*A61B 17/17* (2006.01)
*A61F 2/30* (2006.01)

(56) References Cited

U.S. PATENT DOCUMENTS

2009/0012529 A1* 1/2009 Blain .................. A61B 17/7059
606/99
2015/0005879 A1* 1/2015 Georges .................. A61F 2/447
623/17.11

* cited by examiner

SPINAL FIXATION SYSTEM

FIELD OF THE INVENTION

The invention relates to a spinal fixation system and method of use. In particular, the invention relates, but is not limited, to a spinal fixation system and method of use associated with vertebrae fusion.

BACKGROUND TO THE INVENTION

Reference to background art herein is not to be construed as an admission that such art constitutes common general knowledge in Australia or elsewhere.

Spinal fusion surgery is intended to prevent the movement of painful vertebrae. In particular, spinal fusion surgery limits motion between adjacent vertebrae by creating a fusion environment therebetween.

A common method of stabilising and limiting the motion between adjacent vertebrae is, after the insertion of an intervertebral cage, securing a plate to an anterior face of the adjacent vertebrae. Securing the plate to the vertebrae normally involves screwing fasteners, through apertures in the plate, into prepared holes in the vertebrae.

A problem associated with implantation of the plate is temporarily securing and aligning the plate during the initial plate insertion and screwing of the fasteners. Movement of the plate, either during insertion or fastening, can jeopardise precise placement of the plate. This may lead to further complication including, for example, the fasteners or plate coming into contact with adjacent structures that may, for instance, be neural or vascular.

OBJECT OF THE INVENTION

It is an aim of this invention to provide a spinal fixation system and method of use which overcomes or ameliorates one or more of the disadvantages or problems described above, or which at least provides a useful alternative.

Other preferred objects of the present invention will become apparent from the following description.

SUMMARY OF INVENTION

In one form, although not necessarily the only or broadest form, the invention resides in a spinal fixation system, the system including:
an alignment assembly comprising:
a fastening element; and
a mating element configured to receiving the fastening element thereover and having a releasable connector; and
a fixation assembly comprising:
a plate having an aligning aperture that allows the mating element to be received therethrough; and
an implant configured to be received between adjacent vertebrae and releasably connect with the releasable connector,
wherein the fastening element is configured to move along the mating element to engage with the plate.

Preferably, the fastening element includes an aperture therethrough. Normally, the aperture includes an engagement portion. Typically, the engagement portion engages with the mating element to releasably secure the fastening element as it moves along the mating element.

Preferably, releasably securing the fastening element as it moves along the mating element assists in locking the fastening element in a location relative to the mating element. Preferably, releasably securing the fastening element as it moves along the mating element allows a clamping force to be applied to the plate.

Preferably, the engagement portion is in the form of a thread. In an alternative form, the engagement portion is configured to provide a press fit along the mating element.

Preferably, the fastening element includes an upper body and a lower body. Typically, the upper body includes a driver engagement portion. Normally, the driver engagement portion is a hex head.

Preferably, the lower body includes a plate engagement portion. Typically, the plate engagement portion is configured to engage the plate to centralise the plate about the mating element. Preferably, the plate engagement portion is configured to centralise the plate in a direction between adjacent vertebrae. That is, normally the plate engagement portion is configured to centralise the plate in a longitudinal direction. Normally, the longitudinal direction is in a direction along the spine of a patient.

Preferably, the plate engagement portion includes one or more wing portions. Normally, the one or more wing portions engage with the plate. Normally, the one or more wing portions extend from a central part of the lower portion.

Preferably, the one or more wing portions converge towards an axial axis of the fastening element. Typically, the one or more wing portions linearly converge towards the axial axis of the fastening element. In another form, the one or more wing portions non-linearly converge towards the axial axis of the fastening element.

Preferably, in response to one wing portion engaging with a front and/or rear wall of the aligning aperture in the plate, the plate is configured to shift in a direction towards another wing portion.

Preferably, the mating element includes a body having a first end to receive the fastening element thereover. Normally, the body includes a retaining portion. Typically, the first end is a free end with a cross sectional area substantially the same or smaller than the retaining portion.

Preferably, the retaining portion is configured to engage with the engagement portion to releasably secure the fastening element to the mating element. Typically, the retaining portion extends from at or near the first end towards the releasable connector. Preferably, the retaining portion is in the form of a thread.

Preferably, the body includes a front portion, a rear portion and two side portions. Typically, one or more of the side portions include a substantially flat part. Preferably, the front portion and/or the rear portion include a substantially circular part. Normally, the front portion and/or rear portion include the retaining portion.

Preferably, a distance between the two side portions is smaller than a distance between the front portion and the rear portion. Normally, the distance between the two side portions is substantially the same as a distance between sidewalls in the aligning aperture of the plate. Preferably, the distance between the front portion and the rear portion is smaller than a distance between a front wall and a rear wall in the aligning aperture of the plate.

Preferably, the body includes an aperture therethrough. Typically, the aperture is configured to receive the releasable connector.

Preferably, the releasable connector includes a releasably attaching portion. Normally, the releasably attaching portion releasably connects with the implant. Typically, the releasably attaching portion includes a threaded part. In a further form, the releasably attaching portion press fits into the implant.

Typically, the releasably attaching portion is located below the first end of the body. Normally, the releasably attaching portion is located below the retaining portion of the body. Preferably, the releasably attaching portion is located adjacent to a second end of the body.

Preferably, the releasable connector includes a shaft that is connected between the releasably attaching portion and a head portion. Normally, the head portion is located above the body. Preferably, the head portion is configured to receive a socket. Typically, the head portion includes a hexagonal section.

Preferably, the releasable connector is configured to move relative to the body. Normally, the releasable connector is configured to move between a first position to a second position. Preferably, in the first position, the releasably attaching portion is engaged with the body. Typically, in the second position, the head portion is engaged with the body.

Preferably, the plate includes a first aperture, a second aperture, a third aperture and/or a fourth aperture located about the aligning aperture.

Typically, the first aperture, the second aperture, third aperture and/or fourth aperture are inclined from a top face of the plate to a bottom face of the plate.

Preferably, the bottom face of the plate is configured to be located next to the adjacent vertebrae.

Typically, the implant is a spinal implant. Normally, the implant is in the form of a spinal fusion cage. Preferably, the implant includes a releasable fixing portion.

Preferably, the releasable fixing portion is configured to releasably connect to the releasably attaching portion. Preferably, the releasable fixing portion includes a thread.

In another form the invention resides in an alignment assembly, the alignment assembly including:
  a fastening element; and
  a mating element configured to receive the fastening element thereover at a first end and having a releasable connector with a releasably attaching portion below the first end,
  wherein the fastening element is releasably secured to the mating element as it moves therealong.

Preferably, the releasably attaching portion is located at or next to a second end of a body of the mating element.

Preferably, the alignment assembly is as described herein.

In another form the invention resides in a mating element, the mating element including:
  a body having a first end configured to receive a fastening element thereover; and
  a releasable connector having a releasably attaching portion that is located below the first end,
  wherein the body is configured to releasably secure the fastening element as it moves therealong.

Preferably, the mating element is as described herein.

In another form the invention resides in a method for spinal fixation, the method including the steps of:
  positioning an implant between adjacent vertebrae;
  releasably connecting a mating element to the implant;
  moving a plate along the mating element to be next to the adjacent vertebrae;
  moving a fastening element along the mating element to engage with the plate in order to assist in restricting movement of the plate.

Preferably, the step of connecting the mating element to the implant includes moving the mating element towards the implant whilst it is connected to a first driver.

Typically, the step of connecting the mating element to the implant includes moving a releasably attaching portion along a releasable fixing portion. Normally, the step of moving the releasably attaching portion along the releasable fixing portion includes turning the releasably attaching portion along the releasable fixing portion.

Preferably, the step of moving the plate along the element to be next to the adjacent vertebrae includes substantially engaging sidewalls of an aligning aperture in the plate with side portions of the mating element.

Preferably, the step of moving the fastening element along the mating element to engage with the plate in order to assist in restricting movement of the plate includes first disconnecting the first driver from the mating element.

Normally, the step of moving the fastening element along the mating element to engage with the plate in order to assist in restricting movement of the plate includes moving the fastening element towards the plate whilst it is connected to a second driver.

Preferably, the step of moving the fastening element along the mating element to engage with the plate in order to assist in restricting movement of the plate includes moving an engagement portion of the fastening element along a retaining portion of the mating element.

Typically, the step of moving the engagement portion of the fastening element along the retaining portion of the mating element includes turning the engagement portion along the retaining portion.

Preferably, the step of moving the fastening element along the mating element to engage with the plate in order to assist in restricting movement of the plate includes engaging a first wing of the fastening element with a front wall and/or a rear wall of the aligning aperture in the plate.

Preferably, in response to engaging the first wing of the fastening element with the front wall or rear wall of the aligning aperture in the plate, the method further includes moving the fastening element further along the mating element to engage a second wing of the fastening element with the front wall or rear wall that was not engaged by the first wing.

Preferably, the method further includes preparing holes in the adjacent vertebrae whilst using one or more apertures in the plate as a guide.

Preferably, the method further includes fastening screws into the vertebrae through the one or more apertures in the plate. Preferably, the step of fastening screws into the vertebrae through apertures in the plate includes fastening the screws into said prepared holes of the vertebrae.

Preferably, the method further includes removing the mating element with the first driver whilst the fastening element is connected thereto.

Further features and advantages of the present invention will become apparent from the following detailed description.

BRIEF DESCRIPTION OF THE DRAWINGS

By way of example only, preferred embodiments of the invention will be described more fully hereinafter with reference to the accompanying figures, wherein.

DETAILED DESCRIPTION OF THE DRAWINGS

Figure 1:
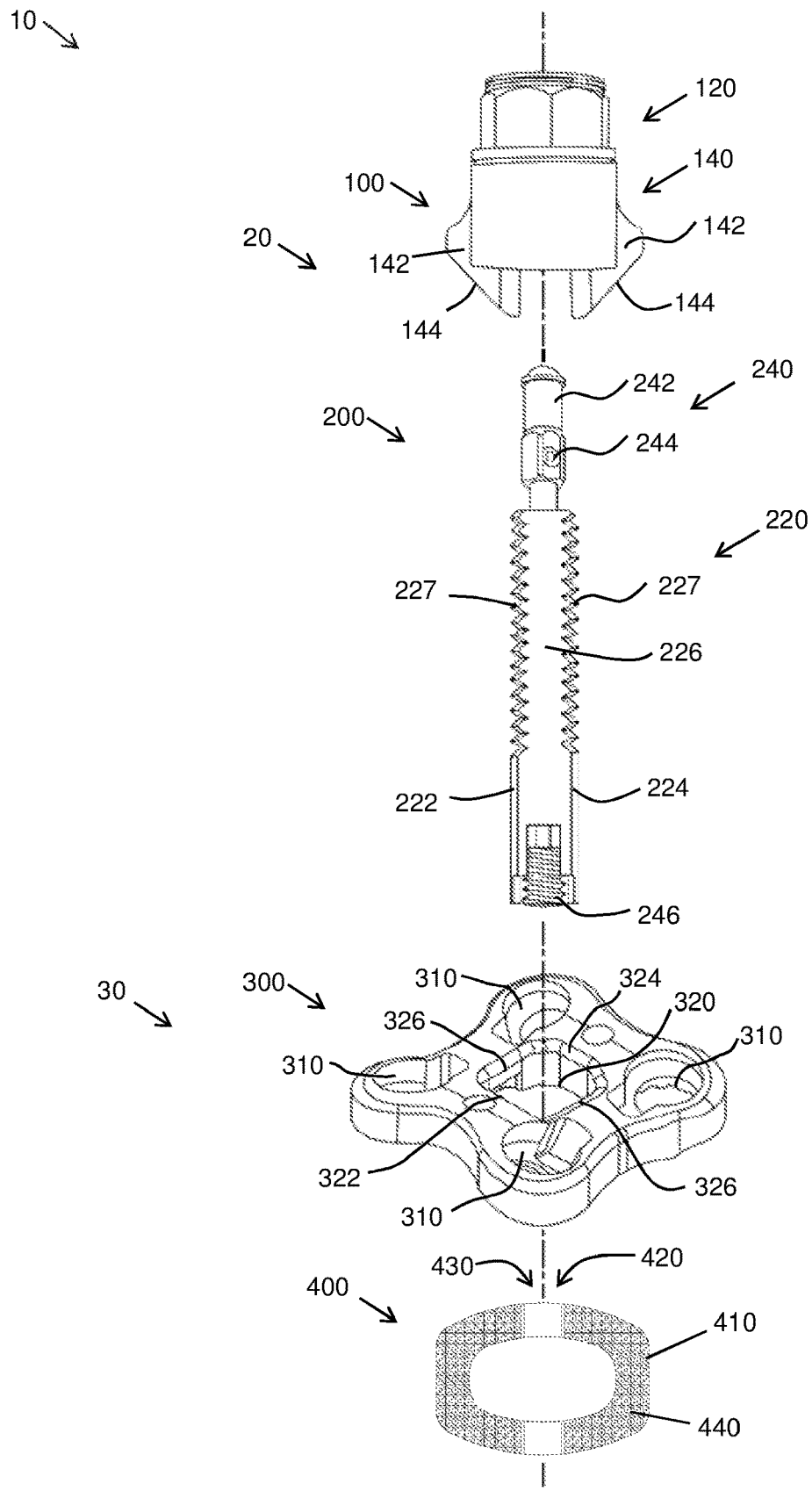
FIG. 1 illustrates a spinal fixation system, according to an embodiment of the invention.

FIG. 1 illustrates a spinal fixation system 10, according to an embodiment of the invention. The spinal fixation system 10 includes an alignment assembly 20 and a fixation assembly 30. As will be appreciated by a person skilled in the art, the fixation assembly 30 in this embodiment remains in a patient after surgery to assist with fusing adjacent vertebrae whilst, as outlined further below, the alignment assembly 20 temporarily assists in aligning components of the fixation assembly 30 during surgery.

The alignment assembly 20 includes a fastening element 100 and a mating element 200. A front view of the fastening element 100, according to an embodiment of the invention, is shown FIG. 2. A cross-sectional view of the fastening element 100, along the line A-A in FIG. 2, is shown in FIG. 3.

Figure 2:
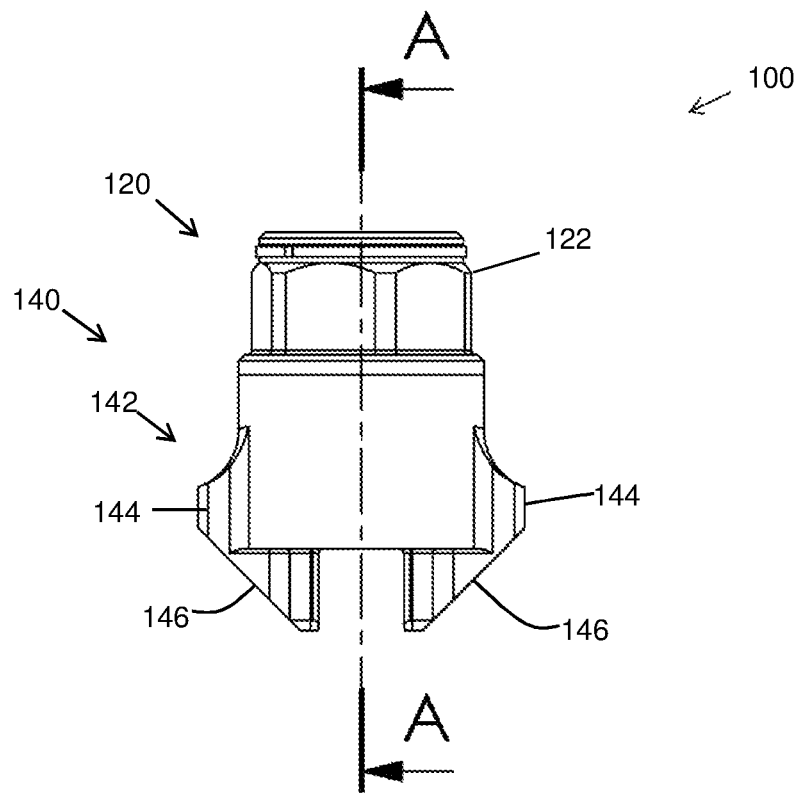
FIG. 2 illustrates a front view of a fastening element, shown in FIG. 1, according to an embodiment of the invention.
Figure 3:
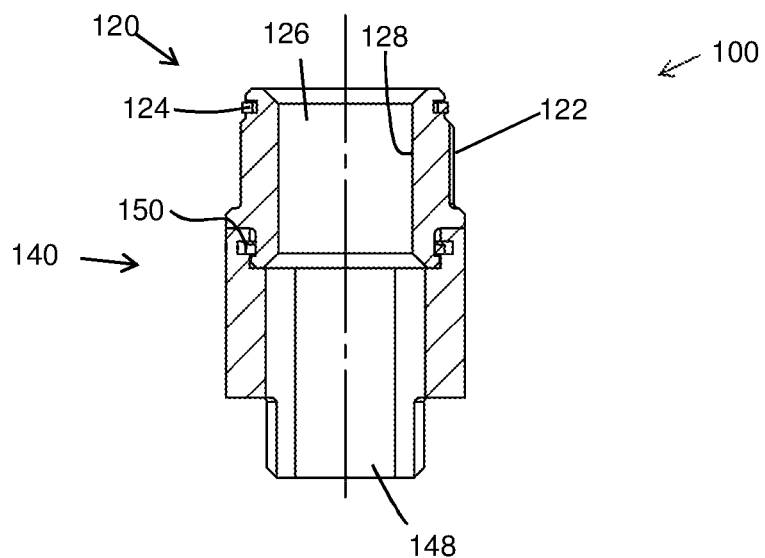
FIG. 3 illustrates a section view of the fastening element shown in FIG. 2.

As shown in FIGS. 2 and 3, the fastening element 100 includes an upper body 120 and a lower body 140. The upper body 120 includes a driver engagement portion 122. In this embodiment, the driver engagement portion 122 is in the form of a hex head. The upper body 120 also includes a clip 124. The clip 124 is a circlip that is located substantially around the upper body 120. As shown further in FIG. 3, the upper body includes an aperture 126 therethrough. The aperture 126 includes an engagement portion 128. It would be appreciated by a person skilled in the art the engagement portion 128 may extend into the lower body 140 or be located in the lower body 140 alone. The engagement portion 128 is in the form of a thread in this embodiment.

The upper body 120 is connected to the lower body 140 via a clip 150 in the form of a circlip. That is, the clip 150 is located between a shoulder on the upper body 120 and a recess located in the lower body 140. It would be appreciated that the upper body 120 and lower body 140 may be releasably connected through other methods including a press fit. In a further embodiment, the upper and lower body 120, 140 may also be integrally formed.

The lower body 140 includes a plate engagement portion 142. The plate engagement portion 142 in this embodiment includes wings 144. The wings 144 include a bearing surface 146 that converges towards an axial axis (e.g. an axis coinciding with section line A-A). In this regard, the bearing surfaces 146 extend transversely to the axial axis. The bearing surfaces 146 are angled at approximately 45 degrees to the axial axis in this embodiment.

The lower body 140 also includes an aperture 148 therethrough which is aligned with the aperture 126. It would is appreciated the apertures 126, 148 collectively define an aperture through the fastening element 100.

Figure 4:
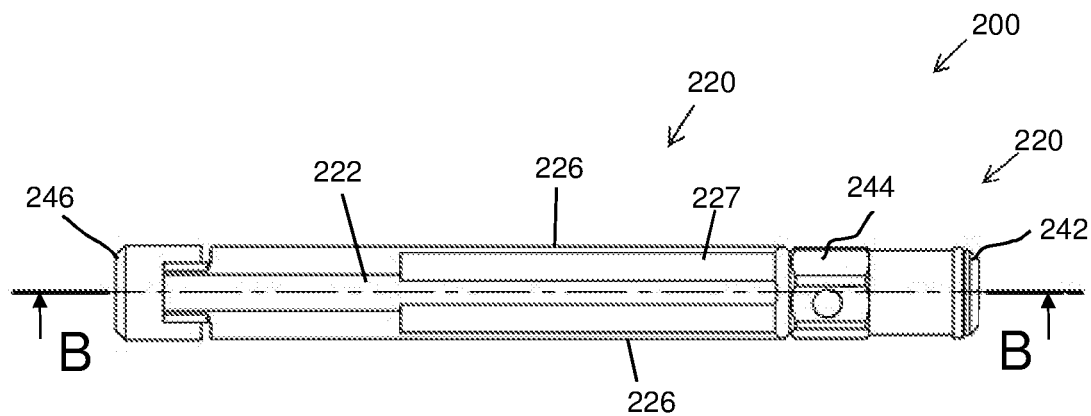
FIG. 4 illustrates a front view of a mating element, shown in FIG. 1, according to an embodiment of the invention.
Figure 5:
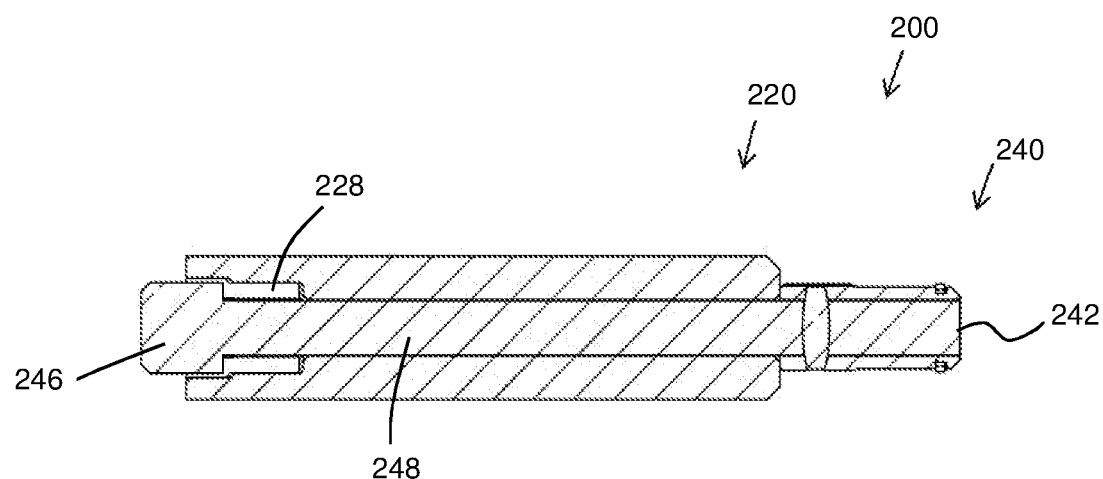
FIG. 5 illustrates a section view of the mating element shown in FIG. 4.
Figure 6:
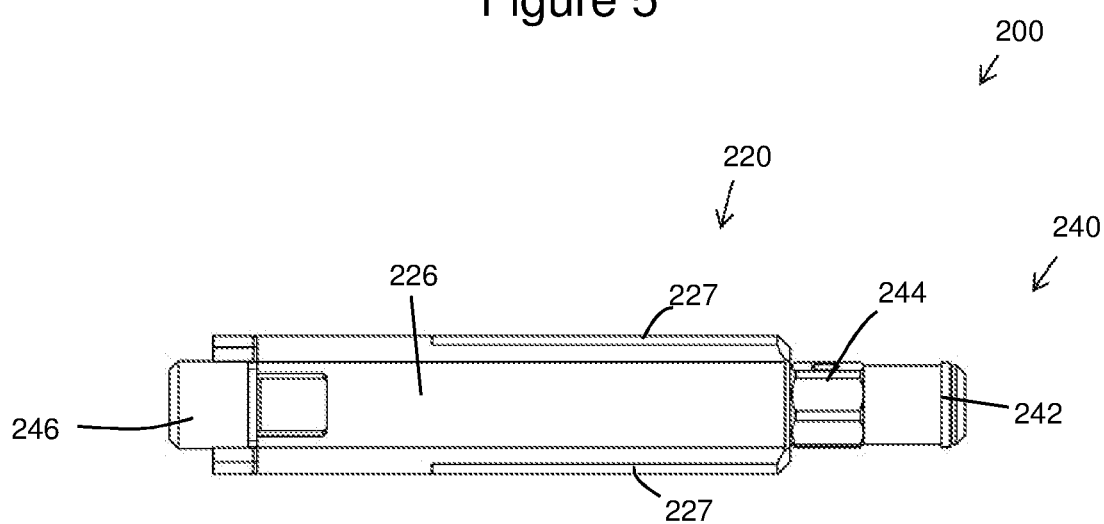
FIG. 6 illustrates a side view of the mating element shown in FIG. 4.

As shown in FIGS. 4 to 6, the mating element 200 includes a body 220 and a releasable connector 240. The body 220 includes a front portion 222, a rear portion 224 and two side portions 226.

The front portion 222 and the rear portion 224 include a substantially circular part in this embodiment. The circular part includes a retaining portion 227 in the form of a thread. The retaining portion 227 is located next to a first end of the body 220. It would be appreciated that the first end of the body 220 is a free end which is shaped the same size or smaller than the retaining portion 227. According, the first end does not provide a barrier or alike to accessing the retaining portion 227 when an object is moved thereover. The retaining portion 227 is configured to engage with the engagement portion 128 to releasably secure the fastening element 100 to the body 220.

The two side portions 226 are substantially flat in this embodiment. The distance between the two side portions 226 is smaller than the distance between the front portion 222 and the rear portion 224.

The body 220 also includes an aperture 228 therethrough. The aperture 228 extends in a longitudinal direction along the body 220. The aperture 228 includes a first cross-sectional area that is smaller than a second cross-sectional area. The releasable connector 224 is received into the aperture 228.

The releasable connector 224 includes a head portion 242 and a releasably attaching portion 246. The head portion 242 includes a driving portion 244. The releasably attaching portion 246 includes a threaded portion. A shaft 248 connects the head portion 242 to the releasably attaching portion 246. The head portion 242 is located above the body 220. The head portion 242 is located adjacent to the first end of the body 220. The releasably attaching portion 246 is located at or near the second end of the body 220.

The cross-sectional area of the head portion 242 and releasably attaching portion 246 is greater than the shaft 248. In this regard, in order to retain the releasable connector 224 in the aperture 228, the head portion 242 and attaching portion 246 are located on either side of the first cross-sectional area of the aperture 228 whilst the shaft 248 extends therealong.

With the above in mind, the releasable connector 224 is configured to move from a first position to a second position. In particular, the releasable connector moves from a first position where the head portion 242 engages the body 220 to a second position where the releasably attaching portion 246 engages a shoulder in the aperture 228 of the body 220.

The fixation assembly 30 includes a plate 300 and an implant 400. The plate 300 includes a plurality of apertures 310. The plurality of apertures 310 include four apertures located near the corners of the plate 300, in this embodiment. The plurality of apertures 310 are inclined from a top face of the plate 300 to a bottom face of the plate 300. The plurality of apertures 310 are configured to receive fasteners (i.e. screws) therethrough, to engage prepared holes in the vertebrae, in order to secure the plate 300 next to the vertebrae. Accordingly, the bottom face of the plate 300 is formed to be located next to the vertebrae.

The plate 300 also includes an aligning aperture 320. The aligning aperture 320 is centrally located in the plate 300 in this embodiment. In this regards, the aligning aperture 320 is located substantially inboard from the apertures 310. The aligning aperture 320 includes front wall 322, rear wall 324 and sidewalls 326. The walls 322, 324, 326 includes an upper gradient surface.

The distance between the sidewalls 326 is substantially the same distance between the side portions 226. Normally, the distance between the front wall 322 and rear wall 324 is larger or smaller than the distance between the front portion 222 and the rear portion 224 but, as outlined further below, this is dependent on the size of the plate 300 and the distance between the adjacent vertebrae.

The implant 400 is in the form of an interbody cage for spinal fusion. The implant 400 includes a body 410 having an aperture 420 therethrough. The aperture 420 includes a releasably fixing portion 430. The body 410 also includes a plurality of ridges 440, on either side of the body 410, that sit adjacent the upper and lower vertebrae.

Figure 7:
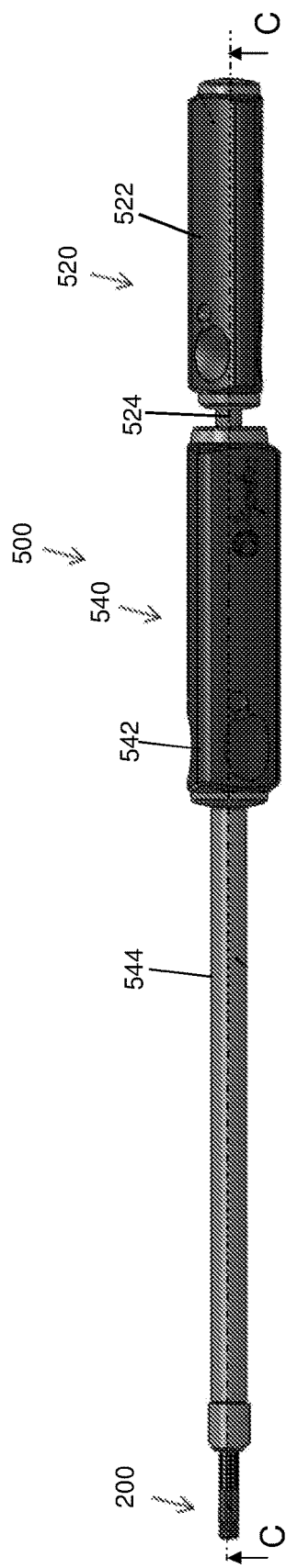
FIG. 7 illustrates a front view of a first driver, according to an embodiment of the invention, with the mating element shown in FIG. 4 connected thereto.
Figure 8:
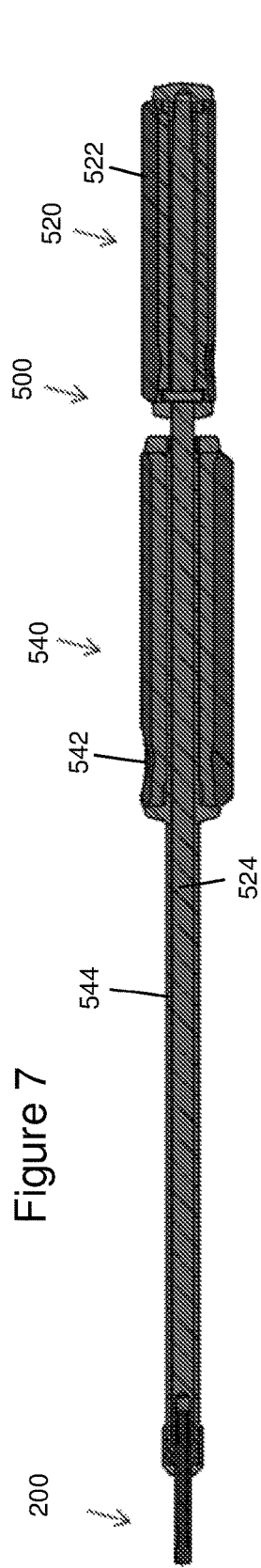
FIG. 8 illustrates a cross section sectional view of the first driver and mating element shown in FIG. 7.

FIGS. 7 and 8 illustrate a first driver 500, according to an embodiment of the invention. The first driver 500 includes an elongate member 520 and a grip 540. The elongate member 520 includes a handle 522 and a shaft 524. The handle 522 is located at one end of the shaft 522 and an aperture is located at another end of the shaft 522. The aperture in the shaft 522 is configured to receive the mating element 200 therein and engage with the driving portion 244. The grip 540 includes a handle 542 and a hollow protrusion 544. The shaft 522 of the elongate member 520 extends through the handle 542 and the hollow protrusion 544. The grip 540 may engage with the retaining portion 227.

Figure 9:
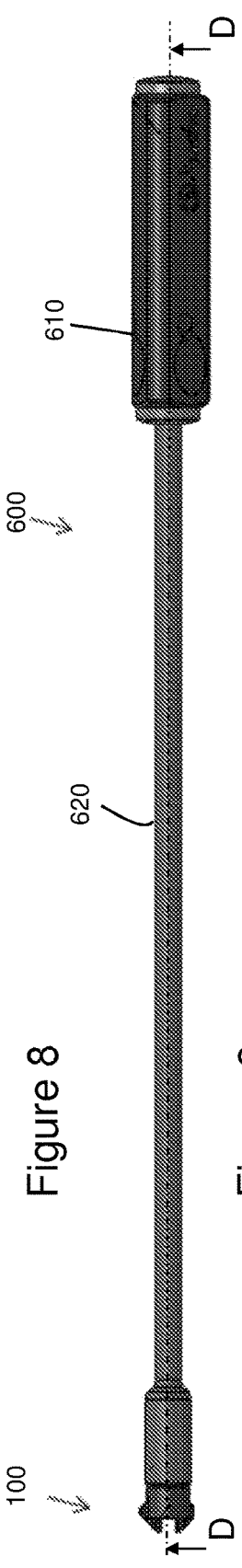
FIG. 9 illustrates a front view of a second driver, according to an embodiment of the invention, with the fastening element shown in FIG. 2 connected thereto.
Figure 10:
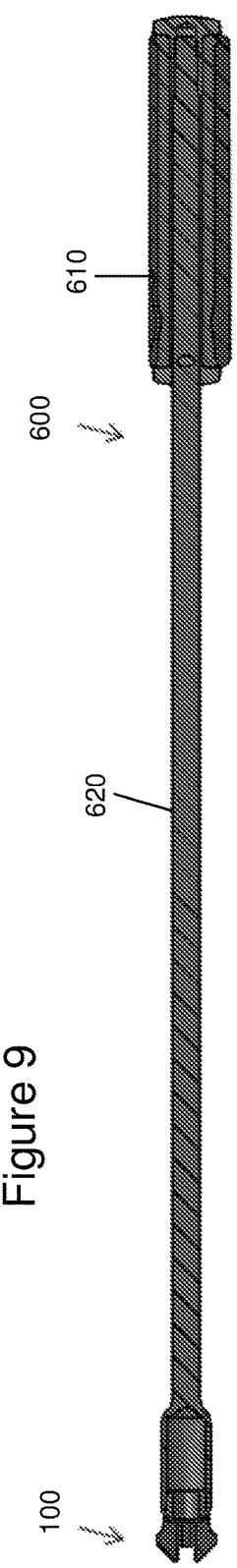
FIG. 10 illustrates a cross section sectional view of the second driver and fastening element shown in FIG. 9.

FIGS. 8 and 9 illustrate a second driver 600. The second driver 600 includes a grip 610 and a shaft 620. The grip 620 is located at one end of the shaft 620 and an aperture is located at another end. The aperture at the end of the shaft 620 is configured to receive the fastening element 100 therein and engaged with the driver engagement portion 122.

In use, a portion of a disc between adjacent vertebrae is removed. Following this, the implant 400 is implanted between the adjacent vertebrae.

To temporarily fasten the mating element 200 with the implant 400, the mating element 200 is first loaded into the first driver 500, as shown in FIGS. 7 and 8. In this regard, the aperture of the shaft 522 receives the driving portion 244.

The releasably attaching portion 246 of the mating element 200 is then inserted and fastened to the releasably fixing portion 430 of the implant 400. It would be appreciated that to fasten the releasably attaching portion 246 to the releasably fixing portion 430, the shaft 522 is rotated, with the mating element 200 at one end, whilst the grip 540 is held relatively fixed.

Once the mating element 200 is releasably fasten to the implant 400, the plate 300 is then moved along (i.e. over) the mating element 200. In the present embodiment, as the plate 300 passes over the mating element 200, the plate 300 is centralised in a first direction (e.g. a lateral direction) between the sidewalls 326 thereof and the two side portions 226 of the mating element 200. This is due to the distance between the two side portions 226 and the sidewalls 326 of the plate 300 being substantially the same.

The plate 300 is moved down along the mating element 200 until it is positioned adjacent to the implant 400. In this regard, the plate 300 is position next to the adjacent vertebrae.

Following the above, the fastening element 100 is moved such that the engagement portion 128 of the fastening element 100 engages the retaining portion 227 of the mating element 200. The fastening element 100 is then moved along the mating element 200 by turning the fastening element 100. It would be appreciated that the fastening element 100 is turned with the second driver 600 which engages the engagement portion 122 of the fastening element 100. As the fastening element 100 moves along the mating element 200, the mating element 200 is received into the aperture of the shaft 620.

The fastening element 100 is moved along the mating element 200 to engage with the plate 300 such that the plate 300 is centralised in a second direction (i.e. a longitudinal direction along the spine). That is, as the fastening element 100 is moving along the mating element 200, a bearing face 146 of one wing 144 will come into contact with either the front wall 322 or rear wall 324 of the plate 300. In response to contacting one of the bearing faces 146 of the wings 144, the plate 300 is shifted in a direction along the wing 144 (i.e. the bearing face 146) as the fastening element 100 is further moved along the mating element 200. This in turn results in plate 300 moving to a centralised location about the mating element 200 and contacting the other wing 144. Once the plate 300 is in contact with both wings 144 (i.e. the bearing faces 146), it is substantially centralised about the mating element 200 and secured in place.

To further elaborate on the above, assuming one of the wings 144 comes into contact with the front wall 322 of the plate 300 first, by way of example, as the fastening element 100 is moved along the mating element 200. This will result in the front wall 322 sliding along the wing 144 which in turn will shift the plate 300 upwards/forwards along the longitudinal axis of the spine. As the fastening element 100 continues to be moved along the mating element 200, the other wing 144 will then come into contact with the rear wall 324 of the plate. As the fastening element is tightened between the plate 300 and mating element 200, the wings 144 will cause the plate 300 to centralise about the mating element 200. That is, the plate 300 is moved into a central position, relative to the mating element 200, in an up and down direction (i.e. longitudinal direction) along the spine.

Once the plate 300 is centralised about the mating element 200, the apertures 310 in the plate 300 are used as guides to prepare holes in the adjacent vertebrae. Following this, screws are then inserted through the apertures 310 into the prepared holes in the adjacent vertebrae. Once the screws are secured, the mating element 200 is then disconnected from the implant 400, normally with the fastening element 100 attached. It would be appreciated that the mating element 200 is disconnected from the implant 400 by rotating the driving portion 244, with the first driver 500, in a direction to release the attaching portion 246 from the releasably fixing portion 430.

The spinal fixation system 10 provides a temporary means for securing and accurately aligning the plate 300 during surgery. In particular, the interaction between the two side portions 226 and the sidewalls 326 centralise the plate 300 in a left to right direction (i.e. a lateral direction) across a patient. Furthermore, the use of the wings 144 allows the plate 300 to be centralised in an up and down direction (i.e. a forward and back direction or a longitudinal direction) along the patient.

With the above in mind, as patients typically range in height and the aligning aperture 320 may change between different plates 300, the wings 144 are able to accommodate these changes in size. For example, a longer aligning aperture 320 will cause the plate to engage further along the wing 144, but this will still allow the plate 300 to be centralised about the mating element 200. Moreover, movement of the plate 300 is minimised during insertion of the plate 300 into the patient, due to its interaction with the mating element 200.

In addition, when the plate 300 is fixed into position, the apertures 310 in the plate 300 may be used as guides in preparing holes in the adjacent vertebrae. The limited movement of the plate 300 also assists in aligning the screws that are inserted into said prepared holes of the patient. This reduces the risk of the screws, plate 300 or alike coming into contact and damaging adjacent structures that may, for instance, be neural or vascular.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step etc.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

In this specification, the terms 'comprises', 'comprising', 'includes', 'including', or similar terms are intended to mean a non-exclusive inclusion, such that a method, system or apparatus that comprises a list of elements does not include those elements solely, but may well include other elements not listed.

The claims defining the invention are as follows:

1. An alignment assembly for aligning and positioning an interbody plate over a disc space in between two adjacent vertebrae, the assembly comprising:
    a fastener having a long axis and a plate engagement comprising opposed wings converging towards said axis; and
    a mate for the fastener configured to receive the fastener thereover at a first end and having a releasable connector with a releasable attachment below the first end;
    wherein the fastener is releasably secured to the mate for the fastener as it moves therealong;
    wherein the mate for the fastener comprises a body having two sides that are substantially flat;
    wherein the body of the mate for the fastener includes an aperture therethrough configured to receive the releasable connector; and
    wherein during use the opposed wings contact one or more edges of an aligning aperture of the interbody plate thereby bringing the interbody plate into alignment with the fastener.

2. The alignment assembly of claim 1 wherein the fastener includes an upper body having a driver engagement.

3. The alignment assembly of claim 1 wherein the fastener includes a lower body having the plate engagement.

4. The alignment assembly of claim 1 wherein said wings comprise respective plate engaging surfaces such that herein in response to one of said wings engaging with a front and/or rear wall forming said edges of the aligning aperture in the plate, the plate is configured to shift in a direction towards the other of said wings.

5. The alignment assembly of claim 1 wherein distance between the two sides is substantially the same as a distance between side walls in the aligning aperture of the plate.

6. The alignment assembly of claim 1 wherein the releasable connector includes a shaft that is connected between a releasable attachment and a head.

7. The alignment assembly of claim 6 wherein the head is located above the body of the mate for the fastener.

8. The alignment assembly of claim 1 further comprising the interbody plate formed with the aligning aperture for receiving the mate for the fastener therethrough.

9. The alignment assembly of claim 8 wherein the plate includes a first aperture, a second aperture, a third aperture and/or a fourth aperture located about the aligning aperture.

10. The alignment assembly of claim 1 further comprising an implant configured to be received between adjacent vertebrae and releasably connect with the releasable connector.

11. A spinal fixation assembly comprising the alignment assembly of claim 10 wherein the implant is in the form of a spinal cage.

* * * * *